(12) United States Patent
Ku et al.

(10) Patent No.: US 6,518,430 B1
(45) Date of Patent: Feb. 11, 2003

(54) PROCESS FOR THE PREPARATION OF 5-(SUBSTITUTED)-10-METHOXY-2,2,4-TRIMETHYL-2,5-DIHYDRO-1H-CHROMENO[3,4-F]QUINOLINES AND DERIVATIVES THEREOF

(75) Inventors: Yi-Yin Ku, Buffalo Grove, IL (US); Timothy A. Grieme, Chicago, IL (US); Padam N. Sharma, Gurnee, IL (US); Prasad S. Raje, Lindenhurst, IL (US); Howard E. Morton, Gurnee, IL (US); Mike A. Fitzgerald, Waukegan, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/960,205

(22) Filed: Sep. 21, 2001

(51) Int. Cl.[7] .................. A61K 31/44; A61K 31/505; C07D 491/00; C07D 311/00; C07D 221/00; C07D 239/00; C07D 455/106
(52) U.S. Cl. ................ 546/152; 546/26; 546/61; 546/62; 546/73; 546/95; 546/152; 514/279; 514/284; 514/285
(58) Field of Search .................. 546/61, 62, 73, 546/95, 152; 514/284, 285, 279

(56) References Cited

FOREIGN PATENT DOCUMENTS

WO          99/41256          8/1999

OTHER PUBLICATIONS

Coghlan et al. (DN 136:102372, HCAPLUS, abstract of WO 2002002565).*

Coghlan et al. (J. Med. Chem. (2001), 44, (18), 2879–2885).*

Elmore et al. (J. Med. Chem. (2001), 44 (25), 4481–4491).*

James P. Edwards et al, "5–Aryl–1, 2–dihydro–5H–chromeno[3,4–f]quinolines as Potent, Orally Active, Nonsterodial Progesterone Receptor Agonists: The Effect of D–Ring Substituents", *J. Med. Chem.*, 1998, vol. 41, p.303–310.

\* cited by examiner

*Primary Examiner*—Sabiha Qazi
(74) *Attorney, Agent, or Firm*—Daniel W. Collins; Cheryl L. Becker

(57) ABSTRACT

The present invention relates to an efficient process for the preparation of 5-(substituted)-10-methoxy-2,2,4-trimethyl-2,5-dihydro-1H-chromeno[3,4-f]quinolines.

15 Claims, No Drawings

PROCESS FOR THE PREPARATION OF 5-(SUBSTITUTED)-10-METHOXY-2,2,4-TRIMETHYL-2,5-DIHYDRO-1H-CHROMENO [3,4-F]QUINOLINES AND DERIVATIVES THEREOF

TECHNICAL FIELD

The present invention relates to an efficient process for the preparation of the selective glucocorticoid receptor agents which are useful 5-(substituted)-10-methoxy-2,2,4-trimethyl-2,5-dihydro-1H-chromeno[3,4-f]quinolines.

BACKGROUND OF THE INVENTION

The glucocorticoid receptor (GR) has an essential role in regulating human physiology and immune response. Steroids which interact with GR have been shown to be potent anti-inflammatory agents. Steroidal GR ligands, however, have side effects associated with chronic dosing believed to be the result of cross-reactivity with other steroid receptors such as estrogen, progesterone, androgen, and mineralocorticoid receptors which have somewhat homologous ligand binding domains. Therefore, nonsteroidal agents selective for GR are actively being researched for the treatment of inflammation, inflammatory disease, immune and autoimmune diseases.

SUMMARY OF THE INVENTION

The present invention is directed to an efficient process for the preparation of 5-(substituted)-10-methoxy-2,2,4-trimethyl-2,5-dihydro-1H-chromeno[3,4-f]quinolines. In particular the present invention is directed to, 5-(allyloxy)-10-methoxy-2,2,4-trimethyl-2,5-dihydro-1H-chromeno[3,4-f]quinoline in an overall yield of 24% and with elimination of all column chromatography purification steps.

DETAILED DESCRIPTION OF THE INVENTION

The present invention is directed to an improved seven-step process that eliminates column chromatography, improves throughput and increases the overall yield for the preparation of (5S) 5-(allyloxy)-10-methoxy-2,2,4-trimethyl-2,5-dihydro-1H-chromeno [3,4-f]quinoline. The improved seven-step process, described in Scheme 2 and more particularly in Examples 1–8, allows for the preparation of (5S) 5-(allyloxy)-10-methoxy-2,2,4-trimethyl-2,5-dihydro-1H-chromeno[3,4-f]quinoline on a larger scale than the processes reported in International Patent Publication No. WO 99/41256 and J. Med. Chem., 41 (1998) 303–310.

The process comprising treating 2-bromo-1,3-dimethoxybenzene, 2-iodo-1,3-dimethoxybenzene or 1,3-dimethoxybenzene with an organolithium reagent in a first solvent at a temperature of about −5° C. to about 15° C., preferably about 0° C. to about 5° C., after complete addition of the organolithium reagent, the temperature is allowed to warm to ambient temperature and the reaction mixture is stirred for about 1 to 4 hours, preferably about 2 hours, recooling the reaction mixture to about 0° C. and then adding $ZnCl_2$ while maintaining the temperature between −5° C. and 15° C., preferably about −5° C. to about 5° C., after complete addition of $ZnCl_2$ allowing the temperature to warm to ambient temperature and allowing the reaction mixture to stir for about 1 to 4 hours, preferably about 2 hours, recooling the reaction mixture to about 0° C. and adding methyl 2-bromo-5-nitrobenzoate, methyl 2-iodo-5-nitrobenzoate or methyl 5-nitro-2-{[(trifluoromethyl)sulfonyl]oxy}benzoate followed by addition of first transition metal catalyst and maintaining the reaction temperature between about 10° C. and about 55° C., preferably between about 20° C. and about 45° C., about 30 minutes after complete addition of first transition metal catalyst adding isopropylacetate and stirring for about 20 to about 90 minutes and then filtering to provide methyl 2',6'-dimethoxy-4-nitro-1,1'-biphenyl-2-carboxylate;

treating 2',6'-dimethoxy-4-nitro-1,1'-biphenyl-2-carboxylate with tribromoborane in a second solvent to provide 1-hydroxy-8-nitro-6H-benzo[c]chromen-6-one;

treating 1-hydroxy-8-nitro-6H-benzo[c]chromen-6-one with a second transition metal catalyst under a hydrogen atmosphere at a pressure of about 20 to about 60 psi, preferably about 40 psi, in a third solvent, preferably N-methylpyrrolidin-2-one (NMP) at a concentration of about 0.5M to about 1.0M, preferably 0.7M, to provide 8-amino-1-hydroxy-6H-benzo[c]chromen-6-one in NMP;

treating 8-amino-1-hydroxy-6H-benzo[c]chromen-6-one in NMP with acetone and iodine and heating the reaction mixture to a temperature of about 95° C. to about 115° C., preferably about 105° C., for about 60 to about 90 hours, preferably 72 hours, allowing the reaction mixture to cool to ambient temperature, filtering, concentrating and then adding ethyl acetate, washing the ethyl acetate solution with 10% sodium thiosulfate, water and then filtering the organics through a pad of celite, adding charcoal to the filtrate and heating the filtrate to reflux for 1 hour, passing the filtrate through a silica gel pad using ethyl acetate, concentrating the filtrate to provide a residue, diluting and reconcentrating the residue about 3 times, drying the residue under reduced pressure, adding acetone and 12M HCl to provide 10-hydroxy-2,2,4-trimethyl-1,2-dihydro-5H-chromeno[3,4-f]quinolin-5-one hydrochloride;

treating 10-hydroxy-2,2,4-trimethyl-1,2-dihydro-5H-chromeno[3 ,4-f]quinolin-5-one hydrochloride with a base and a methylating reagent in a fourth solvent to provide 10-methoxy-2,2,4-trimethyl-1,2-dihydro-5H-chromeno[3,4-f]quinolin-5-one;

treating 10-methoxy-2,2,4-trimethyl-1,2-dihydro-5H-chromeno[3,4-f]quinolin-5-one with a reducing agent in a fifth solvent to provide 10-methoxy-2,2,4-trimethyl-2,5-dihydro-1H-chromeno[3,4-f]quinolin-5-ol;

isolating 10-methoxy-2,2,4-trimethyl-2,5-dihydro-1H-chromeno[3,4-f]quinolin-5-ol;

treating 10-methoxy-2,2,4-trimethyl-2,5-dihydro-1H-chromeno [3,4-f]quinolin-5-ol with allyltrimethylsilane and a Lewis acid to provide 5-(allyloxy)-10-methoxy-2,2,4-trimethyl-2,5-dihydro-1H-chromeno[3, 4-f]quinoline; and Isolating 5-(allyloxy)-10-methoxy-2,2,4-trimethyl-2,5-dihydro-1H-chromeno[3,4-f]quinoline; and resolving 5-(allyloxy)-10-methoxy-2,2,4-trimethyl-2,5-dihydro-1H-chromeno[3,4-f]quinolinem to provide (5S) 5-(allyloxy)-10-methoxy-2,2,4-trimethyl-2,5-dihydro-1H-chromeno[3,4-f]quinoline and (5R) 5-(allyloxy)-10-methoxy-2,2,4-trimethyl-2,5-dihydro-1H-chromeno [3,4-f]quinoline.

As used throughout this specification and the appended claims, the following terms have the following meanings:

The term "acid" as used herein, means an organic or inorganic acid. Representative examples of organic acid include, but are not limited to oxalic acid, tartaric acid, acetic acid, formic acid, trifluoroacetic acid and p-tolouenesulfonic acid. Representative examples of inorganic acid include, but are not limited to, hydrochloric acid (HCl) and hydrobromic acid (HBr). A preferred acid is HCl. A most preferred acid is 12M HCl.

The term "alkyl" as used herein, means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl and tert-butyl.

The term "base" as used herein, means any molecular moiety that can remove the hydrogen from an OH group that is attached to an unsubstituted or substituted phenyl group. Representative examples of base include, but are not limited to, alkoxides such as sodium methoxide, sodium ethoxide, potassium methoxide, potassium ethoxide and potassium tert-butoxide; hydrides such as sodium hydride, potassium hydride and lithium hydride; amides such as lithium diisopropylamide, lithium bis(trimethylsilyl)amide, potassium bis(trimethylsilyl)amide and sodium bis(trimethylsilyl)amide. A preferred base is potassium tert-butoxide.

The term "Lewis acid" as used herein, means a chemical species, other than a proton, that has a vacant orbital or accepts an electron pair. It is to be understood that Lewis acids can be purchased or prepared as complexes including but not limited to, etherates, hydrates, and thioetherates. Representative examples of Lewis acid include, but are not limited to, aluminum chloride, bismuth(III) chloride, boron trifluoride, iron(II) chloride, iron(III) chloride, magnesium bromide, magnesium chloride, magnesium trifluoromethanesulfonate, manganese(II) chloride, zinc bromide, zinc chloride, zirconium(IV) chloride, and the like.

The term "methylating reagent" as used herein, means a reagent that provides an electrophilic source of a methyl group ($CH_3$). Representative examples of a methylating reagent include, but are not limited to, iodomethane, bromomethane, chloromethane, dimethylsulfate and methyl fluorosulfonate. A preferred methylating reagent is dimethylsulfate.

The term "organolithium reagent" as used herein, means an alkyl group, as defined herein, wherein one hydrogen is removed to form a carbanion and the counter cation is lithium. Representative examples of organolithium reagent include, but are not limited to, n-butyllithium, sec-butyllithium, tert-butyllithium and methyllithium. A preferred organolithium reagent is n-butyllithium.

The term "reducing agent" as used herein, means a hydride source that can reduce a lactone to a lactol. Representative examples of reducing agent include, but are not limited to, diisobutylaluminum hydride (DIBAL), lithium aluminum hydride (LAH) and sodium borohydride. A preferred reducing agent is diisobutylaluminum hydride.

The term "first solvent" as used herein, means any organic solvent that will allow the reaction in step (a), the reaction in step (b) and the reaction in step (c) to proceed to completion or substantially to completion. A preferred first solvent is tetrahydrofuran.

The term "second solvent" as used herein, means any organic solvent that will allow the reaction in step (e) to proceed to completion or substantially to completion. A preferred second solvent is methylene chloride.

The term "third solvent" as used herein, means N-methylpyrrolidin-2-one.

The term "fourth solvent" as used herein, means any organic solvent that will allow the reaction in step (1) to proceed to completion or substantially to completion. A preferred fourth solvent is tetrahydrofuran.

The term "fifth solvent" as used herein, means any organic solvent that will allow the reaction in step (n) to proceed to completion or substantially to completion. A preferred fifth solvent is methylene chloride.

The term "first transition metal catalyst" as used herein, means any transition metal catalyst that will allow the reaction in step (c) to proceed to completion or substantially to completion. A preferred first transition metal catalyst is dichloro-bis(triphenylphosphine)palladium(II).

The term "second transition metal catalyst" as used herein, means any transition metal catalyst that will allow the reaction in step (g) to proceed to completion or substantially to completion. A preferred second transition metal catalyst is 5% palladium on alumina.

The term "trialkylsilylalkenyl" as used herein, refers to a $(R_A)(R_B)R_C\text{-}SiR_D$ group wherein $R_A$, $R_B$ and $R_C$ are alkyl and $R_D$ is alkenyl. Representative examples of trialkylsilylalkenyl include, but are not limited to allyl(trimethyl)silane, but-2-enyl(trimethyl)silane and but-3-enyl(trimethyl)silane.

The term "trialkylsilylalkynyl" as used herein, refers to a $(R_E)(R_F)R_G\text{-}SiR_H$ group wherein $R_E$, $R_F$ and $R_G$ are alkyl and $R_H$ is alkynyl. Representative examples of trialkylsilylalkynyl include, but are no limited to trimethyl(prop-2-ynyl)silane, but-2-ynyl(trimethyl)silane and but-3-ynyl(trimethyl)silane.

Synthetic Process

Abbreviations which have been used in the descriptions of the Schemes and the Examples are: t-Bu for tert-butyl; n-BuLi for n-butyllithium; DIBAL or DIBAL-H for diisobutylaluminum hydride; DMF for N,N-dimethylformamide; EtOAc for ethyl acetate; EtOH for ethanol; HPLC for high pressure liquid chromatography; i-PrO for isopropoxy; Me for $CH_3$; MeOH for methanol; NMP for N-methylpyrrolidin-2-one; Pd for palladium; Ph for phenyl; THF for tetrahydrofiran; TLC for thin layer chromatography; and p-TsOH for para-toluenesulfonic acid.

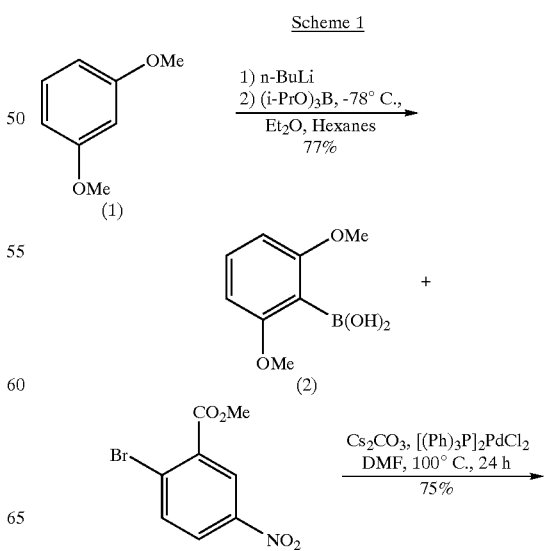

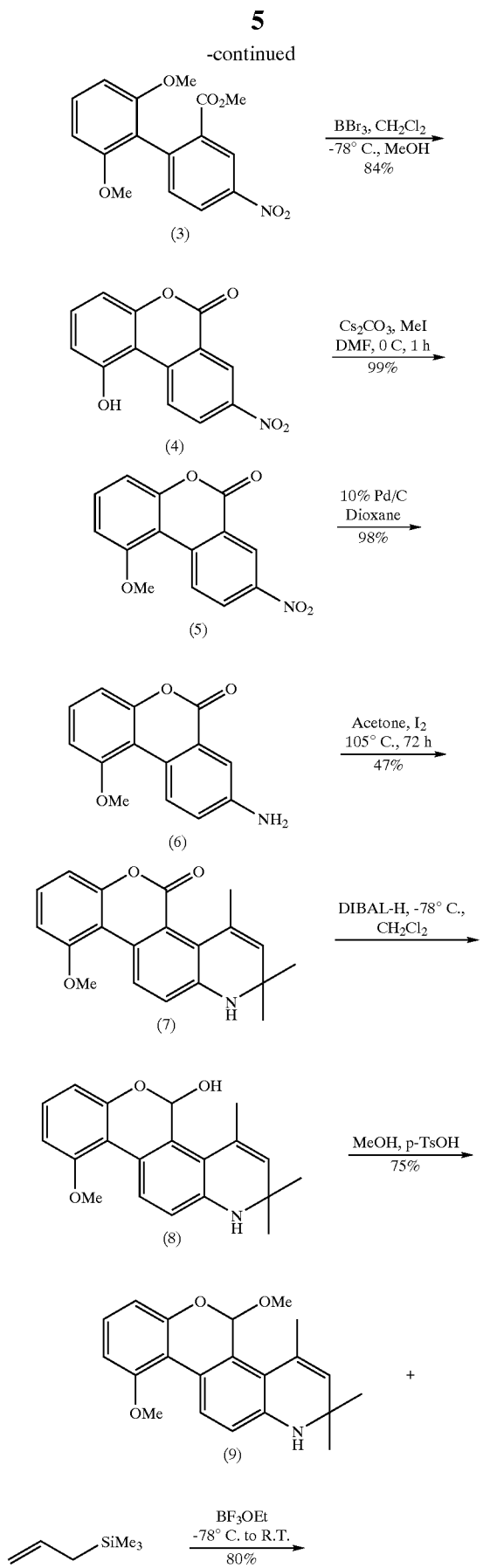

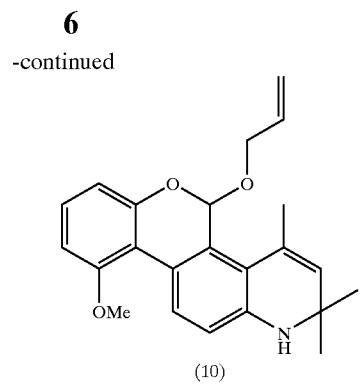

A nine-step route, previously reported in International Patent Publication No. WO 99/41256, that was used for the preparation of smaller quantities of 5-(allyloxy)-10-methoxy-2,2,4-trimethyl-2,5-dihydro-1H-chromeno[3,4-f] quinoline is described in Scheme 1. 1,3-Dimethoxy benzene (1) was first lithiated at −78° C. in hexane and diethyl ether followed by transmetalation with triisopropylborate. Hydrolysis of the boron ester afforded the boronic acid (2) in 77% yield. The boronic acid and commercially available 2-bromo-5-nitrobenzoate were subjected to modified Suzuki coupling conditions to provide the biaryl ester (3) in 75% yield. The biaryl ester was treated with boron tribromide to yield benzocoumarin (4) in 84% yield. The benzocoumarin (4) was methylated with methyl iodide in the presence of cesium carbonate to provide (5). The nitro functionality was reduced to the amino functionality by hydrogenolysis over palladium on carbon in 1,4-dioxane to produce the aniline derivative (6). The aniline derivative (6) was subjected to a modified Skraup reaction with acetone in the presence of iodine at 105° C. for 72 hours to produce the 1,2-dihydro-2,2,4-rimethylquinoline (7) in 47% yield. A similar synthesis of 1,2-dihydro-2,2,4-trimethylquinoline (7) has been previously reported in J. Med. Chem., 41 (1998) 303–310. 1,2-Dihydro-2,2,4-trimethylquinoline (7) was reduced to the lactol (8) with DIBAL followed by methylation with methanol in the presence of p-TsOH to afford the methyl acetal (9) in 75% yield. The methyl acetal (9) was allylated with allyltrimethylsilane in the presence of boron trifluoride etherate to provide 5-(allyloxy)-10-methoxy-2,2,4-trimethyl-2,5-dihydro-1H-chromeno[3,4-f]quinoline in 80% yield. The overall yield for the nine-step process described in Scheme 1 was 13%.

Scheme 2

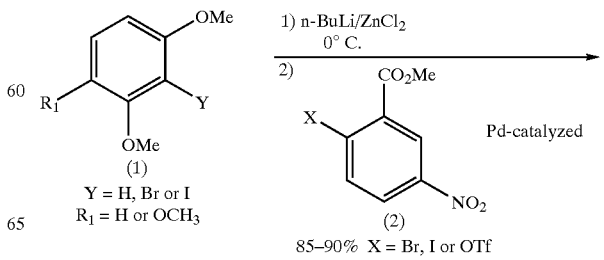

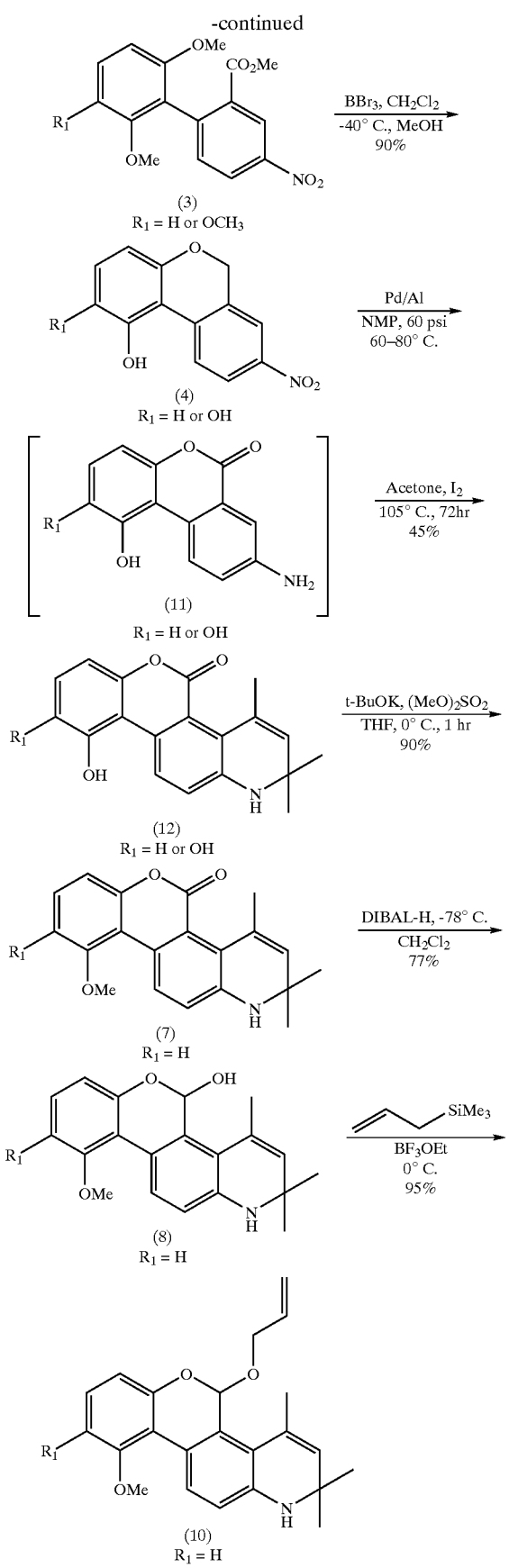

A compound of formula (1), wherein $R_1$ is H ($R_1$ can be $OCH_3$) and Y is H (Y can be Br or I), was lithiated with n-BuLi at 0° C. in THF followed by transmetalation with $ZnCl_2$ to generate the organozinc derivative. The organozinc derivative was reacted directly with a compound of formula (2), wherein X is Br (X can be I or $—OSO_2CF_3$), in the presence of a palladium catalyst such as dichloro-bis (triphenylphosphine)palladium at 45° C. to provide the desired biaryl compound (3), wherein $R_1$ is H, in essentially quantitative yield. The reaction went to completion within two hours and the product precipitated out of the reaction mixture which simplified the isolation and purification to a filtration to provide (3), wherein $R_1$ is H, in high yield (85–90%) and high purity (99%). This procedure increased the reaction yield, improved the throughput and shortened the processing time three fold for the synthesis of the biaryl compound (3), wherein $R_1$ is H. The preparation of the biaryl compound (3), wherein $R_1$ is H, used in Scheme 1 was a two-step process with an overall yield of 58%. The formation of the boronic acid (2), in Scheme 1, required cryogenic reaction conditions and the Suzuki coupling reaction required a long reaction time (24 hours) at high temperature (100° C.) with an excess of cesium carbonate in DMF. In addition, the extractive work-up procedure was very tedious due to a dark colored emulsion which resulted in a very difficult layer separation. Purification of the biaryl product (3), wherein $R_1$ is H, was difficult as isolation of (3), wherein $R_1$ is H, involved repeated washings.

The nitrocoumarin (4), wherein $R_1$ is H, was hydrogenated to the aminocoumarin (11), wherein $R_1$ is H, using 5% palladium on alumina at 60° C. and 40–60 psi in NMP. Using NMP as solvent allowed the reaction concentration to be increased tenfold while reducing the reaction time from 40 hours to less than 2 hours. The reaction mixture was filtered and the filtrate used directly in the next step. The throughput was improved by tenfold and the next step (modified Skraup reaction) could be carried out at double the concentration. In the nine-step procedure described in Scheme 1, the hydrogenation used large volumes of 1,4-dioxane due to the poor solubility of the nitrocoumarin in 1,4-dioxane resulting in longer reaction times (over 40 hours). Also an impractical hot filtration of the palladium catalyst was necessary to avoid precipitation of the aminocoumarin (6) out of the solution.

The filtrate containing aminocoumarin (11), wherein $R_1$ is H, was subjected to modified Skraup conditions and an improved isolation and purification procedure was developed involving an extractive workup procedure. Taking advantage of the solubility differences between the desired product (12), wherein $R_1$ is H, and the by-products, a majority of the by-products were removed with a liquid-liquid extraction (EtOAc/heptane-$H_2O$) and filtration. The purity of the crude product was increased from about 10% potency to more than 75% potency and was further improved to 90% by making a HCl salt. The product (12), wherein $R_1$ is H, can be used directly in the next methylation step without further purification. Isolation and purification of the product of the modified Skraup reaction in Scheme 1 required column chromatography that used large volumes of solvent. One gram of crude product required over one liter of solvent for purification rendering the isolation of large quantities of compound (7) from Scheme 1 as impractical.

The modified Skraup product (12), wherein $R_1$ is H, was then methylated to provide compound (7), wherein $R_1$ is H, as described in Scheme 2. Reordering the sequence of reactions from the order described in Scheme 1 allowed the lower purity modified Skraup product (12), wherein $R_1$ is H, to be methylated resulting in compound (7), wherein $R_1$ is H, which could now be purified by crystallization instead of column chromatography. The crude methylation product with a potency of less than 70% was purified easily by crystallization with EtOAc/heptane to greater than 95% potency.

Compound (7), wherein $R_1$ is H, was treated with DIBAL to provide lactol (8), wherein $R_1$ is H. Lactol (8), wherein $R_1$ is H, can be purified by crystallization from EtOAc/heptane and then can be directly allylated in excellent yield to provide the final product (10), wherein $R_1$ is H. The allylation reaction was carried out at 0° C. under threefold concentrated conditions using two equivalents of allyl (trimethyl)silane instead of four. As a result, formation of the methyl acetal (9) from Scheme 1 and the column chromatography purification steps used to isolate acetal (9) were removed. Also, the column chromatography purification step for the final product (10) was eliminated as well. The final product (10) was crystallized using polar solvents, such as EtOH or iPrOH. Thus, the high purity (>99%) final product was obtained in 95% isolated yield using a filtration procedure.

The present invention is directed to an efficient process for the synthesis of 5-(substituted)-10-methoxy-2,2,4-trimethyl-2,5-dihydro-1H-chromeno[3,4-f]quinolines, in particular 5-(allyloxy)-10-methoxy-2,2,4-trimethyl-2,5-dihydro-1H-chromeno[3,4-f]quinoline, with an overall yield of 24% and elimination of all column chromatography purification steps. The synthesis of the biaryl compound (3), wherein $R_1$ is H, was accomplished in a high yield one-pot procedure. The throughput for the hydrogenation of the nitro coumarin (4), wherein $R_1$ is H, to the aminocoumarin (11), wherein $R_1$ is H, was increased tenfold with use of NMP as the solvent. The isolation of the aminocoumarin (11), wherein $R_1$ is H, was eliminated addressing the issue of the stability of the aminocoumarin intermediate and also enabled the reaction concentration for the modified Skraup reaction to be doubled. The labor-intensive, tedious column chromatography purification step in the modified Skraup reaction was replaced with an efficient extractive work-up procedure. The methylation step was reordered so that the intermediate (7), wherein $R_1$ is H, could be purified by crystallization. A direct allylation of lactol (8), wherein $R_1$ is H, with allyltrimethylsilane was achieved allowing the elimination of methyl acetal formation and its column chromatography purification step as well as increasing the reaction concentration threefold. Finally, a crystalline solid was obtained for 5-(allyloxy)-10-methoxy-2,2,4-trimethyl-2,5-dihydro-1H-chromeno[3,4-f]quinoline (10) making the isolation/purification of (10), wherein $R_1$ is H, practical.

5-(Allyloxy)-10-methoxy-2,2,4-trimethyl-2,5-dihydro-1H-chromeno[3,4-f]quinoline was resolved into its individual (5S) and (5R) enantiomers using the procedure described in Example 8. Resolution techniques well known in the art such as fractional crystallization and the use of chiral auxiliaries can also be used for isolation of the (5S) and (5R) enantiomers.

It is to be understood that the process in Scheme 2 can be used to prepare 9,10-dihydroxy-2,2,4-trimethyl-1,2-dihydro-5H-chromeno[3,4-f]quinolin-5-one.

The present invention is now more particularly described by the following Examples which are not intended to limit the scope the present invention. The present invention covers all alternatives, modifications and equivalents included in the appended claims. Thus, the following Examples illustrate a preferred practice of the invention, it being understood that the Examples are for the purposes of illustration of certain preferred embodiments and are presented to provide what is believed to be the most useful and readily understood description of its procedures and conceptual aspects.

The NMR spectra were recorded on a Varain Unity 500 MHz instrument at 500.5 MHz for $^1$H and 125.9 MHz for $^{13}$C. The electrospray ionization (ESI) and atmospheric pressure chemical ionization (APCI) mass spectra were obtained using a Hewlett Packard 1100, LC-MS, HPLC-mass spectrometer and fast atom bombardment (FAB) mass spectra were obtained using a JEOL SX102A spectrometer. Commercial grade anhydrous solvents and reagents were used without further purification. All reactions were monitored by HPLC (using Zorbax SB-C8, 4.6 mm×25 cm column) with purities being determined by peak area % at 210 and 228 nm.

EXAMPLE 1

Methyl 2',6'-Dimethoxy-4-nitro-1,1'-biphenyl-2-carboxylate

A solution of 1,3-dimethoxybenzene (115.2 ml, 0.88 mol) in anhydrous THF (600 ml) was cooled to 0° C. and treated with n-BuLi (382.4 ml, 0.95 mol, 2.5M solution in hexane) dropwise while maintaining the temperature of the reaction mixture between 0° C. and 5° C. The reaction mixture was allowed to warm to room temperature, stirred for 2 hours and recooled to 0° C. Anhydrous $ZnCl_2$ (141.6 g, 1.04 mol) was added as a solid in portions while maintaining the reaction temperature below 5° C. After adding all the $ZnCl_2$, the reaction mixture was allowed to warm to room temperature and stirred for 2 hours (clear solution). The reaction mixture was recooled to 0° C. and methyl-2-bromo-5-nitrobenzoate (208 g, 0.80 mol) was added as a solid in one portion, followed by the addition of dichloro-bis-(triphenylphosphine) palladium(II) (7 g, 9.90 mmol). Additional THF (200 ml) was added and the reaction mixture was allowed to warm to room temperature. Reaction is exothermic with exotherm starting around 20° C. The reaction mixture was stirred while maintaining the reaction temperature below 45° C. until methyl-2-bromo-5-nitrobenzoate was less than 0.1% peak area detected by HPLC. Solid product started precipitating out typically after 30 minutes. Isopropyl acetate (400 ml) was added and the reaction mixture was stirred for another 30 minutes. The solid was filtered and washed with isopropyl acetate (300 ml), dried at 40° C. under reduced pressure to provide the title compound (203 g, 80%). mp 157° C.; Anal. Calcd. for $C_{16}H_{15}NO_6$: C, 60.57; H, 4.77; N, 4.41; Found C, 60.30; H, 4.76; N, 4.34. $^1$H NMR [$(CD_3)_2SO$] δ 3.65 (3H, s); 3.66 (6H, s), 6.73 (1H, s), 6.77 (1H, s), 7.36 (1H, m), 7.59 (1H, d), 8.36 (1H, dd) and 8.52 (1H, d); $^{13}$C [$(CD_3)_2SO$] δ 52.1, 104.2, 115.7, 123.7, 125.3, 130.1, 133.0, 134.4, 141.4, 146.0, 156.2, 165.6. The $^{13}$C signal for two methoxy groups at 55.6 are overlapping; IR (KBr): 1740 and 1600 cm$^{-1}$; MS (APCI) m/z: 318 (M+H)$^+$, m/z 335 (M+NH$_4$)$^+$, 340 (M+Na)$^+$; FAB-HRMS: found, 318.0989, required 318.0978.

EXAMPLE 2

1-Hydroxy-8-nitro-6H-benzo[c]chromen-6-one

The product from Example 1 (500 g, 1.58 mol) was charged in a flask followed by the addition of $CH_2Cl_2$ (2.1 L). The resulting suspension was cooled to −40° C. with stirring followed by the addition of a $BBr_3$ solution (1.0 M in $CH_2Cl_2$, 3.9 L, 3.9 mol) while maintaining the reaction temperature below −30° C. After complete addition, the reaction mixture was allowed to warm to room temperature and the reaction mixture was assayed for the completion of reaction by HPLC after quenching a small aliquot with MeOH. The reaction mixture was cooled to −40° C. and MeOH (1.2 L) was added slowly to the reaction mixture (plumes of gas start evolving). Evolved gases were scrubbed with water under a stream of $N_2$. Heptanes were then added to the reaction mixture and the thick slurry was allowed to warm to room temperature and stirred for 3–4 hours. Precipitates were then filtered and collected as a pasty material and resuspended in MeOH (3.0 L). Stirring was continued for 6 hours at room temperature and then at −5° C. to 0° C. for 2–3 hours. The slurry was filtered cold and the wet cake washed with cold methanol (150 ml) to afford a bright yellow solid. The wet cake was dried under reduced pressure at 55° C. for 12–16 hours to provide the title compound (397 g, 98%). A small reference sample was obtained by crystallization from DMF/water. mp>260° C.; Anal. Calcd. for $C_{13}H_7NO_5$: C, 60.71; H, 2.24; N, 5.45; Found C, 60.61; H, 2.80; N, 5.37. $^1$H NMR [$(CD_3)_2SO$] δ 6.92(1H, dd), 7.45 (1H, t), 8.63(1H, dd), 8.83(1H, d), 9.27(1H, d), 11.46[1H, s(br)]; $^{13}$C[$(CD_3)_2SO$] δ 105.2, 108.0, 112.6, 121.3, 124.4, 128.8, 128.9, 132.7, 140.1, 145.9, 153.0, 157.7, 159.5.

EXAMPLE 3

8-Amino-1-hydroxy-6H-benzo[c]chromen-6-one

The product from Example 2 (77 g, 89% potency, 0.30 mol) in NMP (425 ml) was treated with 5% Pd on alumina (8.5 g) and the reaction mixture was hydrogenated at 60° C. under 40 psi $H_2$ gas until no $H_2$ uptake was observed, nearly 2.0 hours. After checking for completion of reaction by HPLC the NMP solution was azeo-dried at 40° C. with toluene (1.0 L, then 500 ml). KF of the NMP solution of amine after azeo-drying should be in the range of 0.1–0.8% (mol %). A small reference sample was precipitated out by pouring the NMP solution into cold water and crystallizing the solid from DMF/water. mp>260° C.; Anal. Calcd for $C_{13}H_9NO_3$: C, 68.72; H, 3.99; N, 6.16. Found C, 68.63; H, 3.91; N, 6.17; $^1$H NMR [$(CD_3)_2SO$] δ 5.79[1H, s(br)], 6.82(1H, dd), 7.12(1H, dd), 7.12(1H, t), 7.44(1H, d), 8.83 (1H, d), 10.64[1H, s(br)]; $^{13}$CNMR [$(CD_3)_2SO$] δ 107.3, 107.7, 111.7, 111.8, 121.3 121.4, 122.8, 127.5, 128.6, 149.0, 150.9, 155.4, 161.1.

EXAMPLE 4

10-Hydroxy-2,2,4-trimethyl-1,2-dihydro-5H-chromeno [3,4-f]quinolin-5-one Hydrochloride The NMP solution from Example 3 was diluted with acetone (3.75 L) followed by addition of $I_2$ (33.6 g). The reaction mixture was then divided into three portions and heated in 2.0 L sealed glass reaction vessels at 105° C. for 72 hours. The cooled reaction mixture from six modified Skraup reactions (obtained from two hydrogenation runs) were combined, filtered and analyzed by HPLC (127.7 g of modified Skraup product, 69.9% HPLC potency adjusted yield). This reaction mixture was concentrated to a residual oily material containing NMP. This was diluted with ethyl acetate (1 L) and the organic layer was washed with 10% aqueous sodium thiosulfate (2×1 L), water (2×1 L) and filtered through a pad of celite. The filtrate was treated with charcoal (50 g) and the mixture was heated under reflux for 1 hour. The mixture was then passed through a silica gel pad prepared in heptane. The pad was eluted with ethyl acetate (~1 L). The combined filtrate was concentrated to a residue, dissolved in ethyl acetate (250 ml) and reconcentrated (this procedure was repeated twice). The residue was then dried under reduced pressure to provide a foam. The isolated crude product (172 g, 60.2% potency by HPLC assay, 0.33 mol) was dissolved in acetone (2 L) and concentrated HCl (67 ml, 0.66 mol) was added slowly to form its HCl salt. The mixture was stirred for 3 hours and filtered. The solid was washed with acetone (2×300 ml) and reslurried in acetone (1L) for 1 hour. The solid was filtered, washed with acetone (3×150 ml) and dried at 40° C. under reduced pressure overnight under nitrogen to provide the title compound (99.0 g, 92.24% potency, 45% yield) which was used in the next step without further purification. A small reference sample of the modified Skraup product was obtained as a yellow solid by passing the crude product through a column of silica gel and eluting with ethyl acetate/heptane. mp 242° C.; Anal. Calcd. for $C_{20}H_{19}NO_3$: C, 74.25; H, 5.58; N, 4.56; Found C, 73.98; H, 5.39; N, 4.53. $^1$H NMR [$(CD_3)_2SO$] δ 1.23 (6H, s) 1.94 (3H, d), 3.35 (1H, s), 5.43 (1H, d), 6.76 (1H, m), 6.84 (1H, m), 7.11 (1H, d), 7.17 (1H, m), 8.77 (1H, d) and 10.65 (1H, bs); $^{13}$C NMR [$(CD_3)_2SO$] δ 21.0, 28.0, 49.6, 90.0, 107.0, 114.4, 117.0, 120.4, 121.6, 125.0, 126.6, 127.6, 130.2, 131.2, 131.4, 145.6, 151.0, 155.1, 159.3; IR: 3160, 1720 and 1700 cm$^{-1}$; MS (APCI) m/z: 308 (M+H)$^+$ and 325 (M+NH$_4$)$^+$. HRMS: Found 307.1203, calcd. 307.1208.

EXAMPLE 5

10-Methoxy-2,2,4-trimethyl-1,2-dihydro-5H-chromeno[3,4-f]quinolin-5-one

The crude product from Example 4 (84 g, potency adjusted, 0.24 mol) was suspended in THF (1.0 L) and cooled to 0° C. under $N_2$. Potassium tert-butoxide was added in portions (81.6 g, 0.73 mol) maintaining the internal temperature below 5° C. After stirring for 30 minutes (0° C.), the reaction mixture was treated with dimethyl sulfate (37.5 ml, 0.40 mol) dropwise while maintaining the reaction temperature below 5° C. The reaction was monitored by TLC and/or HPLC until reaction was complete (60 minutes). The reaction was quenched with 50% saturated NH$_4$Cl solution (750 ml) and extracted with EtOAc (750 ml). The organic layer was washed with brine (500 ml), dried over Na$_2$SO$_4$ and concentrated to a crude solid (100.9 g). The crude solid was slurried in methanol (400 ml) and heated at 45° C. until a homogenous suspension was formed. The suspension was then cooled to room temperature, filtered and washed with cold MeOH. The wet cake was dried under reduced pressure at 40° C. to provide the title compound (70.0 g, 99% potent, 89% potency adjusted yield). A small reference sample was recrystallized from MeOH. mp 247–8° C.; Anal. Calcd for $C_{20}H_{19}NO_3$: C, 74.75; H, 5.96; N, 4.36. Found C, 74.38; H, 6.03; N, 4.28. FAB HRMS: calcd m/z for $C_{20}H_{19}NO_3$: 322.1443; Observed m/z: 322.1430. $^1$H NMR (CDCl$_3$) δ 1.33 (6H, s), 2.11 (3H, s), 4.01 (3H, s), 5.57 (1H, s), 6.80 (1H, d), 6.96–6.99 (2H, m), 7.27 (1H,t), 8.70 (1H, d); $^{13}$C NMR (CDCl$_3$) δ 21.2, 28.2, 50.4, 55.8, 77.2, 106.6, 109.2, 109.8, 118.2, 120.2, 124.2, 126.8, 127.2, 127.7, 131.7, 132.0, 144.9, 151.7, 157.5, 160.2. FAB HRMS: calcd for $C_{20}H_{19}NO_3$: 322.1443. Observed 322.1430.

EXAMPLE 6

10-Methoxy-2,2,4-trimethyl-2,5-dihydro-1H-chromeno[3,4-f]quinolin-5-ol

The product from Example 5 (75.2g, 98% potent, 0.23 mol) in CH$_2$Cl$_2$ (3.8 L) under $N_2$ was cooled to −78° C. and treated with 1M DIBAL in heptane (328 ml) dropwise over 1–1.5 hours while maintaining the temperature below −76° C. The reaction was monitored by HPLC and/or TLC until the reaction was complete (1.5 hours). EtOAc (1 L) and a saturated Rochelle salt solution (2 L) was added. The mixture was allowed to warmed to room temperature and stirring was continued until the organic and aqueous layers clearly separated. The organic layer was then washed with brine (0.5L), dried over $Na_2SO_4$ and concentrated to a thick suspension (approx. 300 g). The suspension was then cooled to 0° C., filtered and washed with cold EtOAc. The wet cake was dried under reduced pressure at 40° C. to provide the title compound (59.4 g, 99% potent, 80% potency adjusted yield). A small reference sample was recrystallized from EtOAc. mp 184–5° C.; Anal. Calcd for $C_{20}H_{21}NO_3$: C, 74.28; H, 6.55; N, 4.33. Found C, 73.32; H, 6.51; N, 4.24. $^1$H NMR [$(CD_3)_2SO$] δ 1.08 (3H, s), 1.26 (3H, s), 2.23 (3H, s), 3.86 (3H, s), 5.42 (1H, s), 6.11 (1H, s), 6.56 (1H, d), 6.61 (1H, d), 6.64 (1H, d), 6,71 (1H, d), 6.94 (1H, d), 7.07 (1H, t), 7.99 (1H, d), $^3$C NMR [$(CD_3)_2SO$] δ 22.8, 28.1, 29.9, 49.6, 55.6, 89.8, 105.4, 110.8, 113.0, 113.9, 116.2, 117.0, 126.6, 127.2, 128.2, 130.0, 132.5, 145.4, 150.5, 156.5; FAB HRMS: calcd for $C_{20}H_{21}NO_3$: 323.1521. Observed 323.1514.

EXAMPLE 7

5-(Allyloxy)-10-methoxy-2,2,4-trimethyl-2,5-dihydro-1H-chromeno[3,4-f]quinoline

A three-necked round bottom flask was charged with the product from Example 6 (59.0 g, 0.182 mol) followed by $CH_2Cl_2$ (1.18 L). The resulting suspension was stirred briefly before adding allyltrimethylsilane (58 ml, 0.364 mol) all at once at room temperature. The suspension was cooled to 0° C. under nitrogen and was treated with $BF_3OEt_2$ (46.3 ml, 0.364 mol) dropwise keeping the reaction temperature below 2° C. After complete addition, the mixture was stirred at 0° C. for ~1 hour. The completion of the reaction was monitored with HPLC until the starting material was consumed. The reaction mixture was poured into saturated $NaHCO_3$ solution and stirred for 30 minutes. The organic layer was separated, washed with brine, dried over $Na_2SO_4$, treated with charcoal, filtered and concentrated to an oil. EtOH (200 ml) was added and the solution was concentrated to give a crystalline solid which was suspended with heptane at 0° C. for 2 hours before filtration to give a solid which was dried under reduced pressure at 45° C. to provide the title compound as a light yellow crystalline solid (60.1 g, 95.1%). Anal. Calcd for $C_{23}H_{25}NO_2$: C, 79.51; H, 7.25; N, 4.03; Found: C, 79.26; H, 7.12; N, 3.80, $^1$H NMR [$(CD_3)_2SO$] δ 1.16 (3H, s) 1.17 (3H, s), 2.18 (3H, s), 2.22 (1H, m), 2.46 (1H, m), 3.85 (3H, s), 5.01 (2H, m), 5.44 (1H, br s), 5.77 (1H, dd), 5.82 (1H, m), 6.10 (1H, br s), 6.52 (1H, d), 6.60 (1H, d), 6.70 (1H, d), 7.06 (1H, d), 7.06 (1H, t), 7.96 (1H, d); $^{13}$CNMR [$(CD_3)_2SO$] δ 23.8, 28.8, 28.9, 36.5, 49.7, 55.6, 73.4, 105.6, 110.5, 113.4, 113.4, 116.1, 116.4, 127.3, 117.3, 127.3, 127.7, 132.2, 133.8, 134.5, 145.8, 151.1, 156.4. MS (APCI) m/z: 348 (M+H)$^+$.

EXAMPLE 8

(5S) 5-(Allyloxy)-10-methoxy-2,2,4-trimethyl-2,5-dihydro-1H-chromeno[3,4-f]quinoline and (5R) 5-(Allyloxy)-10-methoxy-2,2,4-trimethyl-2,5-dihydro-1H-chromeno[3,4-f]quinoline The product from Example 7 (1.60 g) was dissolved in ethanol 12 mL) at 45° C. and injected under flow conditions. The first peak was collected from 15 to 23 minutes. Collection was terminated prior to peak trough to prevent co-elution with the second peak. The remaining injections were made at this concentration until racemate was exhausted, 160 g of racemate were chromatographed in 102 injections to provide 73.6 grams of the (S) enantiomer. Preparative HPLC conditions: Chiralcel OJ column, 20 micron silica, 5×50cm, 95:5 hexanes:ethanol; Flow Rate: 117 mL/minute (Nova-sep HPLC, Separation Technologies), Detection: 210 nm, 1 mm path in a Spectra Physics detector. All first peak fractions were pooled and concentrated under reduced pressure with a 40° C. bath to a solid. The product was dissolved in dichloromethane, reconcentrated under reduced pressure and dried under reduced pressure to provide the (S) enantiomer as a light yellow solid, (73.65, >98% ee). Analytical HPLC conditions: Chiralcel OJ 4.6×250 mm, (210 nm); 90:10 hexanes:ethanol; flow rate of 1.0 mL/minute; room temperature; Retention times: (S) enantiomer 13.9 minutes; (R) enantiomer 29.0 minutes.

What is claimed is:

1. A process for the preparation of 5-(substituted)-10-methoxy-2,2,4-trimethyl-2,5-dihydro-1H-chromeno[3,4-f]quinolines or a therapeutically acceptable salt thereof, said process comprising the steps of:

(a) treating a compound selected from the group consisting of 2-bromo-1,3-dimethoxybenzene, 2-iodo-1,3-dimethoxybenzene and 1,3-dimethoxybenzene with an organolithium reagent in a first solvent, followed by addition of $ZnCl_2$, followed by addition of a compound selected from the group consisting of methyl 2-bromo-5-nitrobenzoate, methyl 2-iodo-5-nitrobenzoate and methyl 5-nitro-2-{[(trifluoromethyl)sulfonyl]oxy}benzoate, and followed by a first transition metal catalyst to provide methyl 2',6'-dimethoxy-4-nitro-1,1'-biphenyl-2-carboxylate;

(b) treating said 2',6'-dimethoxy-4-nitro-1,1'-biphenyl-2-carboxylate with tribromoborane in a second solvent to provide 1-hydroxy-8-nitro-6H-benzo[c]chromen-6-one;

(c) treating said 1-hydroxy-8-nitro-6H-benzo[c]chromen-6-one with a second transition metal catalyst under a hydrogen atmosphere at a pressure of about 20 psi to about 60 psi in a third solvent wherein said third solvent is N-methylpyrrolidin-2-one at a concentration of about 0.5M to about 1.0M;

(d) treating the product of step (c) with acetone and iodine in a sealed reaction vessel, heating to a temperature of about 95° C. to about 1 15° C. for about 60 hours to about 90 hours to provide 10-hydroxy-2,2,4-trimethyl-1,2-dihydro-5H-chromeno[3,4-f]quinolin-5-one;

(e) treating said 10-hydroxy-2,2,4-trimethyl-1,2-dihydro-5H-chromeno [3,4-f]quinolin-5-one with a base and a methylating reagent in a fourth solvent to provide 2,2,4-trimethyl-10-(methyloxy)-1,2-dihydro-5H-chromeno[3,4-f]quinolin-5-one;

(f) treating said 2,2,4-trimethyl-10-(methyloxy)-1,2-dihydro-5H-chromeno [3,4-f]quinolin-5-one with a reducing agent in a fifth solvent to provide 2,2,4-trimethyl-10-(methyloxy)-2,5-dihydro-1H-chromeno [3,4-f]quinolin-5-ol; and (g) treating said 2,2,4-trimethyl-10-(methyloxy)-2,5-dihydro-1H-chromeno[3,4-f]quinolin-5-ol with a silyl compound selected from the group consisting of trialkylsilylalkenyl and trialkylsilylalkynyl, followed by addition of a Lewis acid to provide said 5-(substituted)-

10-methoxy-2,2,4-trimethyl-2,5-dihydro-1H-chromeno[3,4-f]quinoline.

2. The process according to claim 1 further comprising resolving said 5-(substituted)-10-methoxy-2,2,4-rimethyl-2,5-dihydro-1H-chromeno[3,4-f]quinoline to provide (5S) 5-(substituted)-10-methoxy-2,2,4-trimethyl-2,5-dihydro-1H-chromeno[3,4-f]quinoline and (5R) 5-(substituted)-10-methoxy-2,2,4-trimethyl-2,5-dihydro-1H-chromeno[3,4-f]quinoline.

3. The process according to claim 1 wherein said organolithium reagent is n-butyllithium and said first solvent is tetrahydrofuran.

4. The process according to claim 3 wherein after complete addition of said $ZnCl_2$ in step (a), warming to ambient temperature, stirring for about 2 hours and recooling to about 0° C.

5. The process according to claim 4 wherein said first transition metal catalyst is dichloro-bis(triphenylphosphine)palladium(II).

6. The process according to claim 5 wherein said second solvent is methylene chloride.

7. The process according to claim 6 wherein said second transition metal catalyst is palladium on alumina.

8. The process according to claim 7 wherein said acid is hydrochloric acid.

9. The process according to claim 8 wherein said base is potassium tert-butoxide, said methylating reagent is dimethyl sulfate and said fourth solvent is tetrahydrofliran.

10. The process according to claim 9 wherein said reducing agent is 1M diisobutylaluminum hydride in heptane and said fifth solvent is methylene chloride.

11. The process according to claim 10 wherein said silyl compound is trialkylsilylalkynyl.

12. The process according to claim 10 wherein said silyl compound is trialkylsilylalkenyl.

13. The process according to claim 10 wherein said silyl compound is allyl(trimethyl)silane.

14. The process according to claim 13 wherein said Lewis acid is boron trifluoride.

15. The process according to claim 14 further comprising resolving 5-(allyloxy)-10-methoxy-2,2,4-trimethyl-2,5-dihydro-1H-chromeno[3,4-f]quinoline to provide (5S) 5-(allylxoy)-10-methoxy-2,2,4-trimethyl-2,5-dihydro-1H-chromeno[3,4-f]quinoline and (5R) 5-(allyloxy)-10-methoxy-2,2,4-trimethyl-2,5-dihydro-1H-chromeno[3,4-f]quinoline.

\* \* \* \* \*

UNITED STATES PATENT AND TRADEMARK OFFICE
CERTIFICATE OF CORRECTION

PATENT NO.     : 6,518,430 B1  
DATED          : February 11, 2003  
INVENTOR(S)    : Yi-Yin Ku et al.

It is certified that error appears in the above-identified patent and that said Letters Patent is hereby corrected as shown below:

<u>Column 14,</u>
Line 50, replace "1 15 C" with -- "115 C" --.

Signed and Sealed this

Fifteenth Day of April, 2003

JAMES E. ROGAN
*Director of the United States Patent and Trademark Office*